(12) United States Patent
Roehn et al.

(10) Patent No.: US 10,842,922 B2
(45) Date of Patent: Nov. 24, 2020

(54) CONTAINER FOR A HEART PUMP DEVICE AND METHOD FOR OPERATING A HEART PUMP DEVICE

(71) Applicant: ECP ENTWICKLUNGSGESELLSCHAFT MBH, Berlin (DE)

(72) Inventors: Daniel Roehn, Berlin (DE); Joerg Schumacher, Teltow (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 277 days.

(21) Appl. No.: 15/543,006

(22) PCT Filed: Jan. 12, 2016

(86) PCT No.: PCT/EP2016/050487
§ 371 (c)(1),
(2) Date: Jul. 12, 2017

(87) PCT Pub. No.: WO2016/113266
PCT Pub. Date: Jul. 21, 2016

(65) Prior Publication Data
US 2018/0001008 A1    Jan. 4, 2018

(30) Foreign Application Priority Data

Jan. 13, 2015   (EP) .................................... 15150897

(51) Int. Cl.
*A61M 1/12*    (2006.01)
*A61M 1/10*    (2006.01)
(Continued)

(52) U.S. Cl.
CPC .......... *A61M 1/125* (2014.02); *A61M 1/1008* (2014.02); *A61M 1/1024* (2014.02);
(Continued)

(58) Field of Classification Search
CPC .. A61M 1/125; A61M 1/1088; A61M 1/1024; A61M 1/122; A61M 1/1034;
(Continued)

(56) References Cited

U.S. PATENT DOCUMENTS 4,216,860 A * 8/1980 Heimann ............ A61M 25/002
206/364
5,660,273 A * 8/1997 Discko, Jr. .......... A61M 35/003
206/15.3
(Continued)

FOREIGN PATENT DOCUMENTS

| CN | 103957957 A | 7/2014 |
| WO | WO 2013/165683 A1 | 11/2013 |
| WO | WO-2014/164136 A1 | 10/2014 |

OTHER PUBLICATIONS

International Search Report—PCT/EP2016/050487, dated Apr. 4, 2016.
(Continued)

*Primary Examiner* — Chun Hoi Cheung
(74) *Attorney, Agent, or Firm* — Botos Churchill IP Law LLP

(57) ABSTRACT

The invention relates to a container (1, 1', 1") for a heart pump device (4, 8, 12, 17, 18, 19, 26) with a first receiving space (3) for a compressible and expandable heart pump (4), wherein the first receiving space is delimited on several sides, in particular on all sides, by one or more closure elements (5, 5', 6, 6' 6") and is closed off to the outside for preventing a contacting of the heart pump, wherein the closure elements (5, 5', 6, 6' 6") leave free an opening (7) for the passage of a catheter (8) from the outside into the first receiving space (3), wherein the diameter of the opening (7) is dimensioned such that the heart pump can pass this exclusively in a condition which is at least partly compressed compared to the expanded condition. For implanta-
(Continued)

Figure 1:
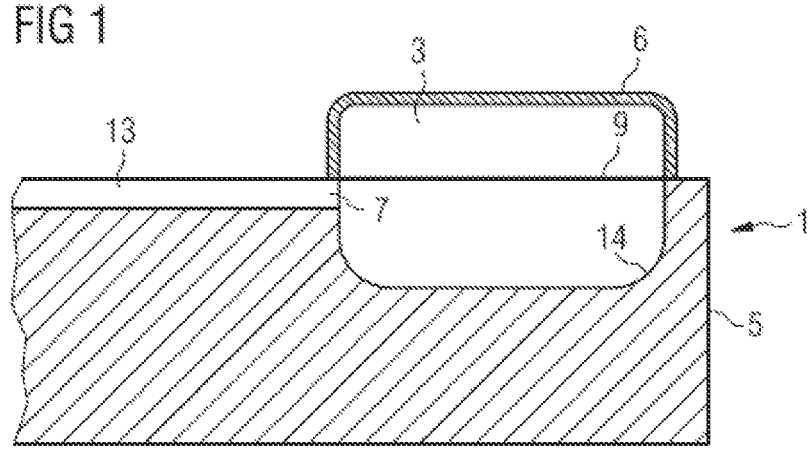

tion, the heart pump in the container (1, 1', 1") can firstly be operated by trial in the container (1, 1', 1") whilst feeding a rinsing fluid and can then be pulled through the opening (7) amid simultaneous compression, into a sheath element (11).

19 Claims, 5 Drawing Sheets

(51) Int. Cl.
*B65D 75/32* (2006.01)
*B65D 75/52* (2006.01)

(52) U.S. Cl.
CPC .......... *A61M 1/1034* (2014.02); *A61M 1/122* (2014.02); *B65D 75/322* (2013.01); *B65D 75/52* (2013.01); *A61M 1/1001* (2014.02); *A61M 1/101* (2013.01); *A61M 2205/70* (2013.01); *A61M 2209/06* (2013.01)

(58) Field of Classification Search
CPC .............. A61M 1/1001; A61M 1/101; A61M 2205/70; A61M 2209/06; B65D 75/322; B65D 75/52
USPC ........................................ 206/581, 438, 571
See application file for complete search history.

(56) References Cited

U.S. PATENT DOCUMENTS

| | | | | |
|---|---|---|---|---|
| 6,068,121 A * | 5/2000 | McGlinch | ........... | A61M 25/002 206/364 |
| 6,105,761 A * | 8/2000 | Peuker | ................... | B65D 75/58 206/15.3 |
| 6,328,159 B1 * | 12/2001 | Discko, Jr. | .......... | A61M 35/003 206/209 |
| 6,685,013 B2 * | 2/2004 | Discko, Jr. | .......... | A61M 35/003 206/209 |
| 6,779,657 B2 * | 8/2004 | Mainwaring | .......... | B65D 25/08 206/15.3 |
| 7,097,075 B2 * | 8/2006 | Peuker | ............... | B65D 81/3266 206/221 |
| 7,320,398 B2 * | 1/2008 | Bertl | ...................... | B65D 75/36 206/15.3 |
| 7,374,040 B2 * | 5/2008 | Lee | ......... | B65D 75/32 206/209 |
| 8,181,777 B2 * | 5/2012 | Suchan | ................ | B65D 75/323 132/317 |
| 9,144,481 B2 * | 9/2015 | Walter | ............... | B65D 81/3266 |
| 9,434,522 B2 * | 9/2016 | Leiner | .................. | B65D 75/327 |
| 2003/0135086 A1 | 7/2003 | Khaw et al. | | |
| 2004/0243214 A1 * | 12/2004 | Farrell | .................. | A61F 2/0095 623/1.11 |
| 2008/0045861 A1 * | 2/2008 | Miller | .................. | A61B 10/025 600/567 |
| 2010/0230285 A1 | 9/2010 | Ross et al. | | |
| 2011/0027750 A1 * | 2/2011 | Boehm | .............. | B65D 81/3294 433/89 |
| 2014/0110296 A1 * | 4/2014 | Terzibashian | ....... | A61M 25/002 206/438 |
| 2015/0352316 A1 * | 12/2015 | Terzibashian | .......... | B65D 43/16 206/363 |

OTHER PUBLICATIONS

Office Action from corresponding Chinese Application No. 201680009047.1 dated Jul. 1, 2020 (10 pages).
Office Action from corresponding Japanese Application No. 2017-537228 dated Jul. 7, 2020 (9 pages).

* cited by examiner

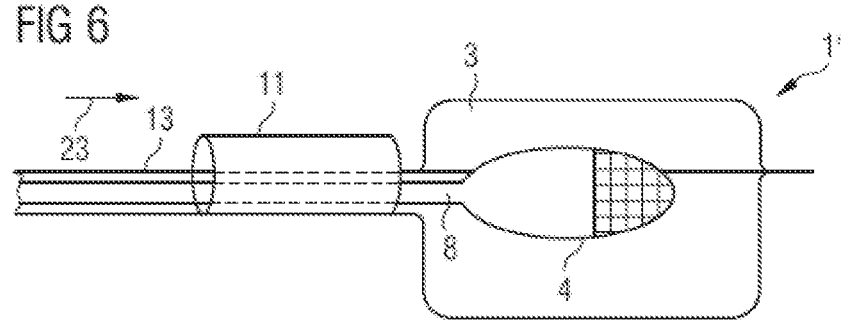
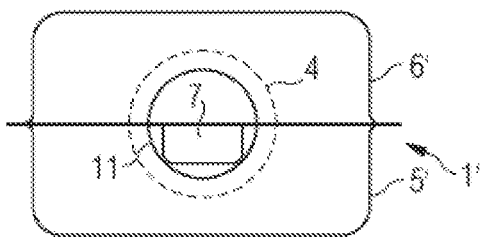
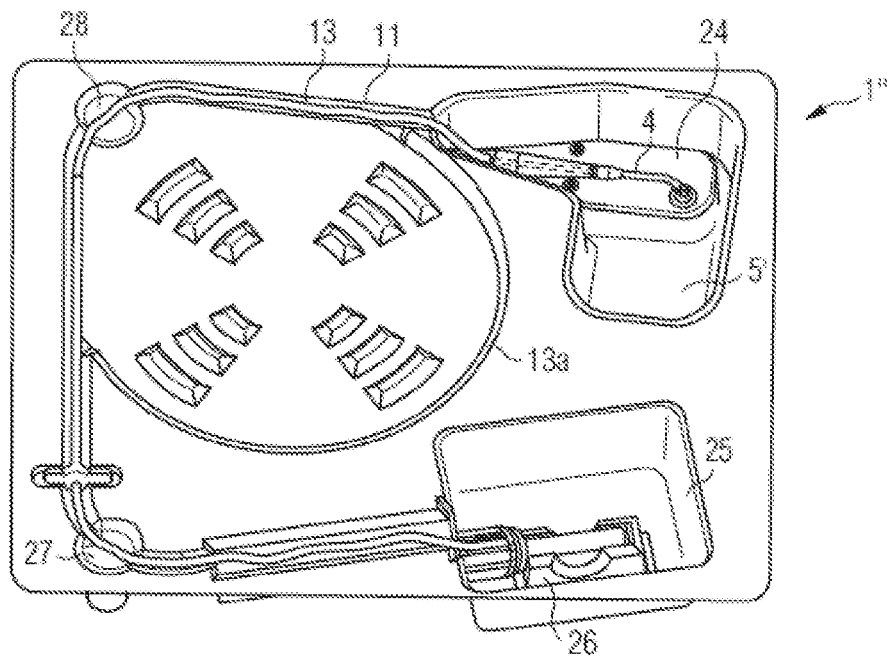

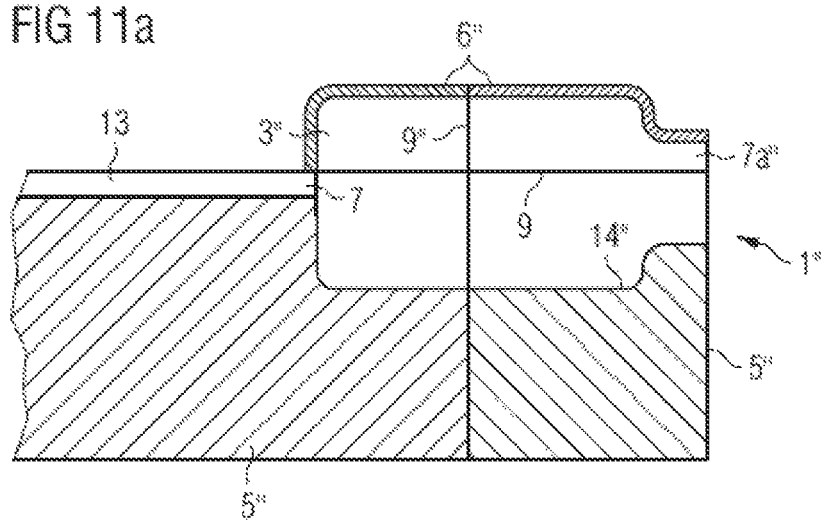
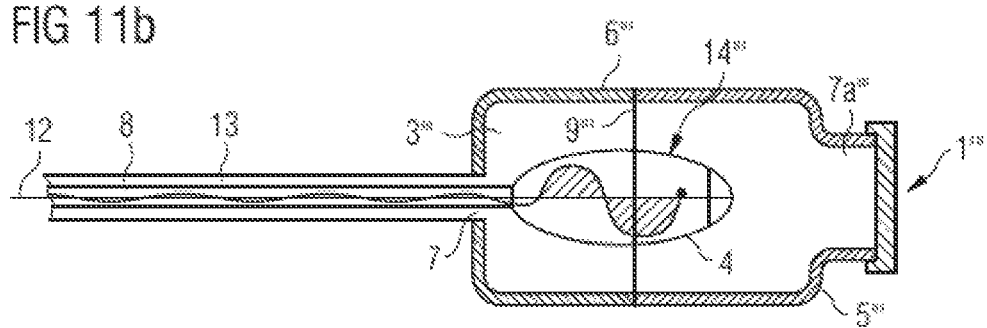

US 10,842,922 B2

CONTAINER FOR A HEART PUMP DEVICE AND METHOD FOR OPERATING A HEART PUMP DEVICE

CROSS-REFERENCE TO RELATED APPLICATIONS

This application is a United States National Stage filing under 35 U.S.C. § 371 of International Application No. PCT/EP2016/050487, filed Jan. 12, 2016, which claims the benefit of European Patent Application No. 15150897.5, filed Jan. 13, 2015, the contents of all of which are incorporated by reference herein in their entirety.

The invention lies in the field of mechanics and engineering which is to say precision engineering and can advantageously be applied in the field of medical technology. The invention is particularly directed to an advantageous packaging for a heart pump device.

Mechanical heart pumps have been increasing applied in more recent times for assisting or also for the replacement of the heart activity of a patient. Basically, such pumps are operated within or outside the body of a patient. However, in many cases it is desirable to implant such pumps into the body of a patient.

In this context, pumps which can be compressed and expanded to a very large extent so that they can be implanted with small dimensions and be expanded in the body of the patient are already known. One special type of such pumps comprises a drivable rotor which delivers blood in the axial direction, wherein the rotor with a pump casing can preferably be brought into the region of a ventricle or aorta and be operated there. The transport of such pumps into the body of a patient can be effected for example through a blood vessel up to the heart.

Of course, a reliable sterility is necessary with the manufacture, transport and the preparation for implantation, of such heart pump systems. This can be at risk if parts of the heart pump device are not professionally and carefully removed from a sterile packaging. In particular, the implanted parts must be protected from contact with objects outside the body of the patient. Contamination with fluff for example can also greatly compromise the functioning of such pumps, and an incorrect contact with the hands can cause critical damage under certain circumstances.

It is the object of the present invention, against this background, to provide a container for a heart pump device which reliably protects the parts of the heart pump device, keeps them sterile and permits a removal with reduced risks of contamination.

According to the invention, this object is achieved by the features of the independent patent claim 1 or 2. Designs are specified in the dependent claims.

The invention accordingly, amongst other things, specifically relates to a container for a heart pump device with a first receiving space for a compressible and expandable heart pump, wherein the first receiving space is delimited on several sides, in particular on all sides, by one or more closure elements and is closed off to the outside for preventing a contact of the heart pump, wherein the closure elements leave free an opening for the passage of a catheter from the outside into the first receiving space, wherein the diameter of the opening is dimensioned such that the heart pump can pass this exclusively in a condition which is at least partly compressed compared to the expanded condition.

A heart pump device accordingly comprises at least one compressible and expandable heart pump as well as further parts as the case may be, such as a catheter and/or a catheter rinsing device for example, and a drive shaft which runs within the catheter and is for the heart pump, and yet further parts as the case may be.

A container should be provided for such a heart pump device. This container comprises a first receiving space, in which the heart pump can be accommodated in a manner such that it is protected from contact by the closure elements, for example by the operating personnel. Thereby, the closure elements can close off the closure space in a fluid-tight manner with the exception of the opening for the passage of a catheter. However, one can also envisage the closure elements comprising openings, and one of the closure elements for example being constructed in a grid-like manner. An optical control of the heart pump located in the first receiving space can be rendered possible by way of this for example. However, at least a part of the closure elements at least partly can be designed in an optically transparent manner, in order to permit a viewing into the first receiving space.

The opening for the passage of a catheter serves for leading through a catheter which is directly connected to a heart pump, wherein advantageously the complete length of the catheter has space outside the first receiving space in a second receiving space of the container. Finally, a grip which is arranged on the catheter for handling can have space in a third receiving space of the container and there for example be likewise surrounded on all sides by walls of the container.

The diameter of the opening should be dimensioned such that the pump cannot pass the opening in the expanded condition on removal (the opening could firstly be larger on packaging and would then not be closed by a cover until afterwards). For example, one can envisage the pump in the expanded condition being mounted in the first receiving space, in order to be able to taken into operation there for testing. A rotor of the pump can for example be set into rotation by way of a drive shaft which runs through the catheter, in order to test the operationally readiness of the heart pump. The limited size of the opening ensures that the heart pump in this expanded condition cannot be simply removed from the first receiving space, for example pulled out by way of the catheter. Here, what is decisive is rather the fact that the pump or the pump head cannot be contacted by hand. The risk of an inadvertent contact with the heart pump is further reduced with this. Due to the dimensioning of the opening, it is ensured that the heart pump is at least partly compressed on withdrawing this out of the first receiving space, so that it can be pulled directly into a sheath which is applied on the outer side of the first receiving space in the region of the opening and which receives the pump at least in the partly compressed condition. One can envisage the diameter of the opening being smaller than 6 mm, preferably smaller than 5 mm, particularly smaller than 4 mm.

One advantageous design of the container according to the invention envisages at least the closure elements, in particular the complete container, consisting essentially of a plastic material, in particular a plastic foil. The container can be manufactured for example as a so-called blister of flexurally rigid plastic foil. However, a thicker plastic material can be provided, or parts of the container can consist of plastic elements which are manufactured in an injection moulding method. If the container consists essentially of a blister, then it can be formed from a plastic foil with the deep-drawing method or with the pressing method.

A further advantageous design of the invention envisages the first receiving space being delimited essentially by two half-shell-like closure elements which are joined together. The receiving space for example can comprise a first half-shell in the form of a trough for receiving the heart pump, said trough partly delimiting the first receiving space, and at least one further closure element as a half-shell can be placed upon the first half-shell, in order to completely close off the first receiving space. The second half-shell, which thus forms a cover, can be connected to the first half-shell by way of pressing, bonding, welding or any other joining methods, and advantageously cannot be detached without destruction. By way of this, it can be ensured that a heart pump which on the part of the manufacturer is arranged in the receiving space and which before its application for implantation, is still located in this first receiving space, cannot have been removed from this in the meantime.

The invention can thus envisage the closure elements being connected to one another in a non-releasable manner or in a difficultly releasable manner.

The two half-shells can be placed onto one another with openings facing one another or with a corresponding alignment of the openings.

Moreover, one can advantageously envisage the opening being formed for the passage of a catheter between two closure elements or being open towards the joining location between two closure elements. The insertion of the heart pump and the catheter connected to this, into an opening before joining together several closure elements for delimiting the first receiving space is possible in a particularly simple manner by way of this.

As mentioned above, one can advantageously envisage a first of the closure elements being designed as part of a blister which receives at least one catheter, in particular additionally further parts of the heart pump device.

One can moreover envisage the first closure element in the region of the first receiving space forming a capture shell for fluid. With this, the wetting of the heart pump in the first receiving space with a fluid for a test operation is simplified. The wetting is moreover advantageous for a damage-free compressing of the pump. The fluid for example can be supplied via the catheter to the heart pump. The capture shell ensures that the fluid on the one hand collects around the pump and thus the wetting of the heart pump is ensured, and on the other hand that it does not escape out of the first receiving space in an uncontrolled manner.

The invention can advantageously also be designed by way of the opening at least partly consisting of a cylinder-symmetrical channel. Such a cylinder-symmetrical channel with preferably smooth walls permits a heart pump to be pulled through with a simultaneous compression, without harming the casing of the heart pump. Thereby, one can preferably envisage the cylinder-symmetrical channel narrowing outwards from the inside of the first receiving space, and having no sharp edges in the region which the pump passes.

The cylinder-symmetrical channel for this purpose can for example be designed in a conical or sectionwise conical manner. The channel for example at its run-out to the inside of the first receiving space can comprise an introduction funnel, into which the heart pump can be pulled amid at least partial compression.

It can moreover be advantageous for the run-out of the opening to the outer side of the closure elements and of the first receiving space to comprise an edge, on which a hollow-cylindrical sheath element displaceable along the catheter can be supported in the axial direction of the channel.

A sheath in the form of a hollow-cylindrical component, in particular a peel-way sheath for example, which can be removed radially by way of destruction on tearing open, can be pulled over the catheter which is to say this can be pulled into the sheath, and is usually already a constituent of the heart pump device located in the container. Such a sheath element can be pressed from the outer side of the first receiving space against the edge of the opening on the closure elements, so that the heart pump can be pulled out of the first receiving space through the opening and pulled into the sheath element, by way of the catheter which runs through the sheath element. Thereby, the heart pump is at least partly radially compressed already within the opening of the receiving space and in particular is compressed even further radially on entry into the sheath element. However, one can also envisage the inner diameter of the sheath element corresponding to the diameter, to which the heart pump is compressed already in the opening of the receiving space, so that a further compression on pulling into the sheath is done away with. The edge of the opening can advantageously have an annular surface which runs perpendicularly to the longitudinal axis of the opening.

When the heart pump is pulled into the sheath element, then the heart pump device can be removed from the container and be introduced into the body of a patient by way of an introduction sheath. For this, the sheath element is coupled onto the introduction sheath, and the heart pump is displaced out of the sheath element into the introduction sheath. If the sheath element is designed as a peel-away sheath, then this can be removed without any problem after the introduction of the heart pump into the introduction sheath. However, the sheath element itself can be used as an introduction sheath, by way of the sheath element with the pump compressed therein, being introduced into the patient, for example via a guide wire. A separate lumen for the guide wire is to be provided for this.

The invention moreover, apart from a container of the type described above, also relates to a container in the corresponding embodiment with a heart pump device, wherein a compressible and expandable heart pump is located in the first receiving space and wherein a catheter which is connected to the heart pump projects through the opening out of the first receiving space, wherein in particular a sheath element through which the catheter passes is provided in a freely displaceable manner on this.

The invention moreover relates to a method for the operation of a heart pump device, with which a heart pump is arranged in a first receiving space of a container according to one of the claims 1 to 17, and for example is externally driven in rotation by a shaft running through a catheter to the heart pump (a pump with an integrated motor on the pump head is however also possible). This method permits the functional capability of a heart pump provided with a rotor to be tested already when in the container, without the danger of contact and de-sterilisation arising. The test operation usually takes place at speeds below the operating speed in the patient body, for example at 50%, in particular also only at 30% or 10% of the speed at the most.

For this, one can also advantageously envisage a fluid being delivered to the heart pump along the catheter through an opening provided on the catheter. With this, it is ensured that the heart pump is tested in contact with a fluid under realistic conditions. The heart pump device can simultaneously be filled as much as possible with fluid, so as to largely avoid enclosures of air on implantation. Any biocompatible rinsing fluid, for example saline solution, glucose solution or likewise can be considered as fluid which is delivered to the heart pump.

The invention moreover relates to a method for the operation of a heart pump device, with which a heart pump is arranged in the first receiving space of a container according to one of the claims 1 to 17, wherein the heart pump is connected to a catheter which projects through the opening out of the first receiving space, characterised in that the heart pump, by way of the catheter, is pulled through the opening out of the first receiving space amid radial compression and pulled into a sheath element which is freely displaceable on the catheter in the axial direction (which is to say in the longitudinal direction of the catheter).

The objects which are specified in the independent claims, amongst other things include one or more closure elements delimiting a receiving space for a compressible and expandable heart pump. "Receiving space" is preferably to be understood as the smallest coherent space which completely encloses the pump head of a heart pump (further parts connecting for example to a removal opening 7 (see figures below) are not to belong to this). This is effected for preventing a contacting of the heart pump, i.e. the heart pump is protected from contact in the receiving space. The closure elements leave free at least one opening for the passage of a catheter, wherein the diameter of the opening is dimensioned such that the heart pump can pass this exclusively in a condition in which is at least partly compressed compared to the expanded condition. Hereby, "for passage of the catheter" is to be understood in that a corresponding catheter passes this opening, and preferably is not to be understood as a certain passage direction. One speaks of "one or more closure elements" in the independent claims. In particular in the case of "several closure elements", these can have different designs. This means that the closure elements which form the receiving space can be joined to one another in a different manner. Thus connections can be realised e.g. as screw connections, etc. The joining is preferably such that this cannot be released without destruction, but can alternatively also be manufactured in a destruction-free manner. With this, an expanded pump can be accommodated in the receiving space for example, by way of these closure elements being joined together "around the pump" and thereafter no longer being able to be separated from one another in a destruction-free manner. In this context, a joining line which connects different closure elements to one another can be arranged either in the longitudinal direction of catheter projecting out of the opening of the receiving space, or also orthogonally to this direction. Further details are specified hereinafter concerning this.

In an embodiment, the first receiving space is delimited by at least two closure elements which are joined along a joining line, wherein the joining line runs in a cross section of the receiving space which is larger than the cross section of the opening for the passage of a catheter. In this manner, it is possible for the closure elements to be joined "around the pump head", and a later withdrawal of the heart pump (of the pump head) is only possible amid compression.

A further embodiment envisages the receiving space comprising more than one opening. For this, it is possible for example for the compressible and expandable heart pump to be pulled into the receiving space such that the bringing of the expandable heart pump into the receiving space can be effected essentially without compression. However, the removal of the pump head (preferably at the opposite end of the receiving space) is then only possible under compression (see for example FIG. 11a).

A further development envisages at least one of the openings of the receiving space being closed by a cover which is joined onto this opening of the receiving space, in a manner removable without destruction or also with destruction. Thus for example it is possible in the manner described above, for a pump to firstly be pulled through the larger opening (which does not necessarily force a compression of the heart pump) into the receiving space. It is subsequently possible to close this by way of a cover, in a manner such that the cover cannot be released in a destruction-free manner. In this manner, it is ensured that the heart pump cannot be removed by the user out of the receiving space without compression.

It is also possible to provide the receiving space with openings such that the heart pump device/the heart pump/the pump head are introducible into the receiving space without compression, but can only be removed exclusively in a condition which is at least partly compressed compared to the expanded condition.

Figure 2:
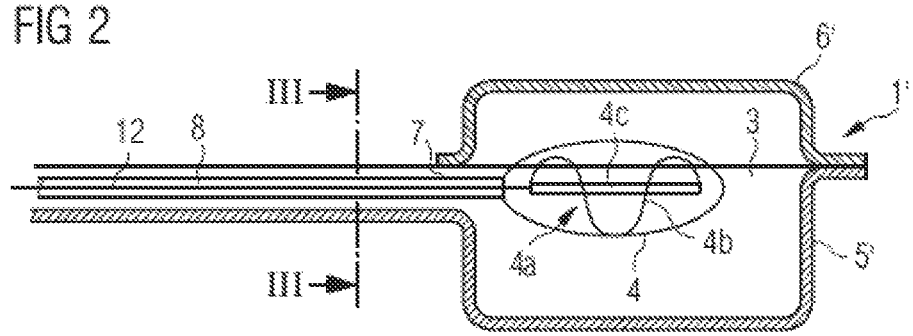
Figure 3:
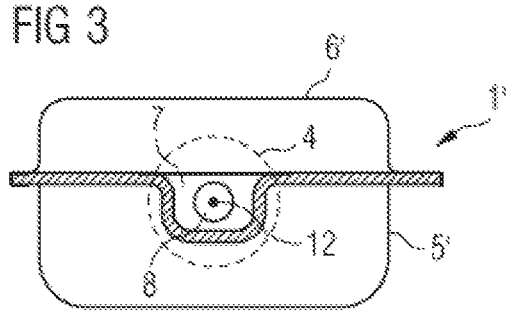
Figure 4:
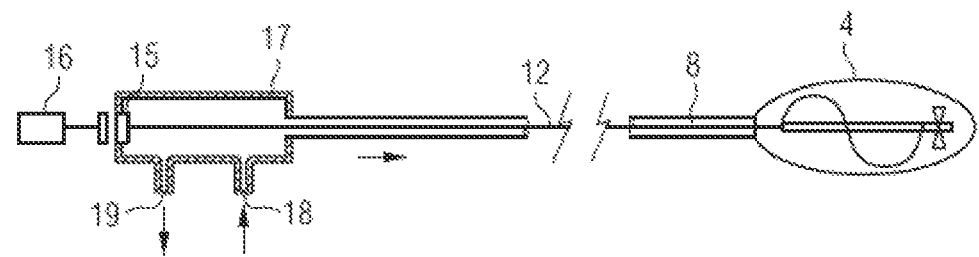
Figure 5:
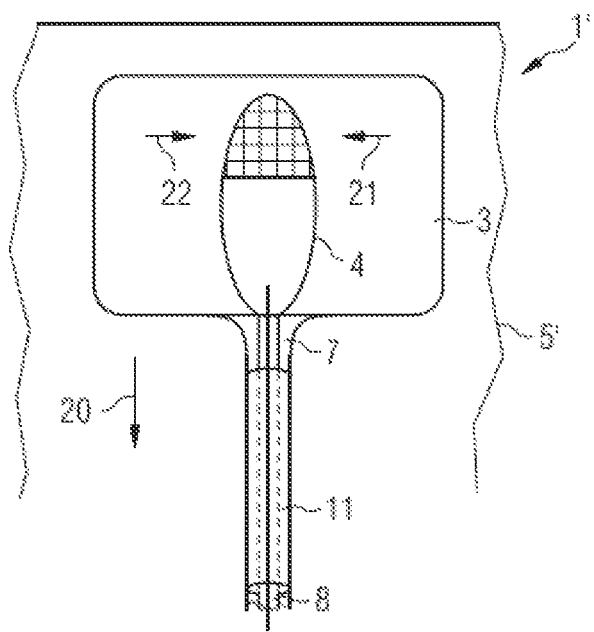
Figure 9:
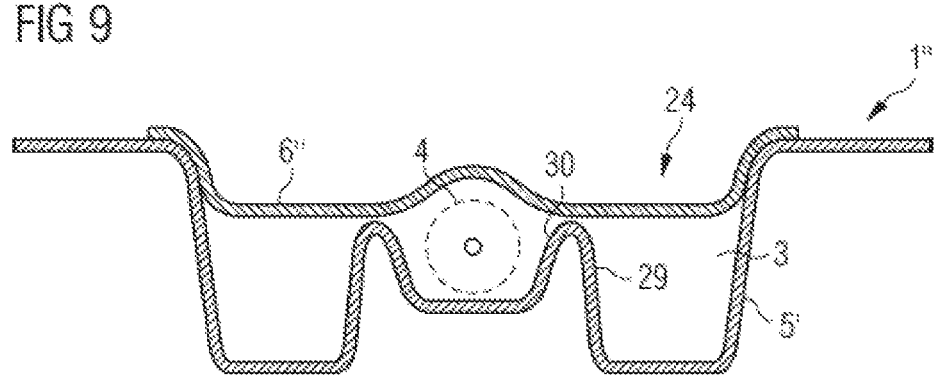
Figure 10:
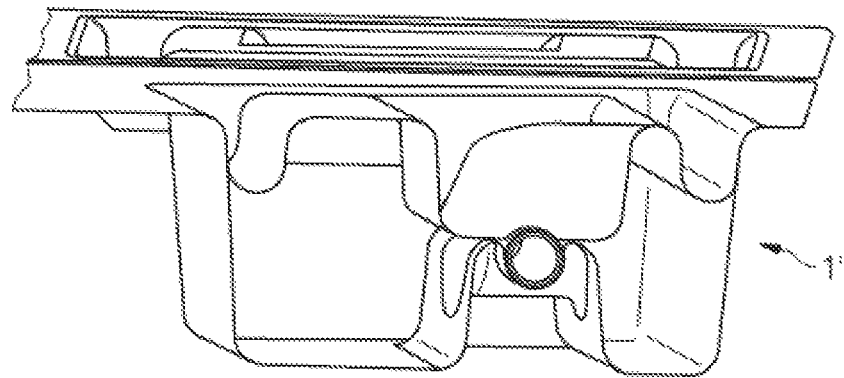

The invention is hereinafter represented by way of an embodiment example in the figures of a drawing and described hereinafter. Thereby are shown in:

FIG. 1 in a cross section, a container according to the invention, in a schematic manner, FIG. 2 a cross section of the container according to the invention, with a heart pump, FIG. 3 a container in a further cross section, FIG. 4 a heart pump with a catheter, FIG. 5 a plan view onto a container with a heart pump, FIG. 6 a cross section through a container with a heart pump and with a sheath element, FIG. 7 a different cross section through a container as well as a sheath element, FIG. 8 a three-dimensional view of a container in the embodiment as a blister, FIG. 9 a cross section through a container which is designed as a blister FIG. 10 a detail of a container which is designed as a blister, in a three-dimensional view as well as FIGS. 11a and 11b cross sections or part cross sections of further embodiments of container according to the invention.

FIG. 1 in a cross section shows a container 1 with two closure elements 5, 6, wherein the first closure element 5 is designed as a solid body, wherein the second closure element 6 as a thin-walled half-shell in the form of cover closes the first receiving space 3. An opening 7 is provided in the region of the closure elements 5, 6, and specifically specially as a recess in the first closure element 5, through which recess a catheter can exit from the first receiving space 3 into the outer space. A groove 13 which can run annularly in the further course of the container 1 can be provided for receiving the catheter, in order to permit the depositing of one or more loops of a catheter. This solid representation of the first closure element 5 is only given by way of example, in order to explain the basic function.

The first closure element 5 should form a fluid-tight capture basin 14, into which a heart pump can be inserted and which can capture fluid for a test operation.

The second closure element 6 is preferably non-releasably connected and sealingly connected to the first closure element 5 in the region of the joining location 9, wherein the connection can advantageously be designed also in a fluid tight manner with the exception of the opening 7, but not in an airtight manner (since the air here should escape from the catheter). The joining location 9 with this example forms a joining line or an annular joining surface which as a whole lies in a plane here.

The second closure element 6 can be designed in a fluid-tight manner as a bent, flat plastic part, preferably as a stiff foil, but it can also comprise openings and/or one or more optical windows, in order to permit the viewing into the first receiving space 3. What is decisive for the second closure element 6 is that it protects the heart pump which is to be kept in the first receiving space 3, from contact.

A container 1' with which the first closure element 5' just as the second closure element 6' is designed as a stiff foil in the form of a blister is shown in FIG. 2. The first receiving space 3 is formed just as with the embodiment example in FIG. 1, and a heart pump 4 which is arranged in the first receiving space 3 is represented schematically in FIG. 2. The heart pump 4 comprises a rotor 4a with a spiral-shaped delivery element 4b and a hub 4c, wherein the hub 4c is connected to a drivable flexible drive shaft 12. The drive shaft 12 runs out of the heart pump 4 through a catheter 8 which passes the opening 7.

The heart pump 4 is represented in the non-compressed condition, in which its radial extension perpendicular to the axial direction indicated by the hub 4c is larger than the extension of the opening 7.

A section which is already indicated and represented at III in FIG. 2 is represented in FIG. 3, with a view onto the first closure element 5' and the second closure element 6' as well as the opening 7, wherein the catheter 8 with the drive shaft 12 is drawn in, and wherein the outline of the heart pump 4 is drawn in a dashed manner. It is evident from FIG. 3 that the diameter of the heart pump 4 is larger than the clear width of the opening 7, so that the heart pump 8 on the catheter 8 can only be pulled through the opening 7 out of the first receiving space 3 amid simultaneous radial compression.

FIG. 4 shows a heart pump device with a heart pump 4 which has already been described by way of FIG. 2, as well as with a catheter 8 and with a drive shaft 12, wherein moreover the drive-side end of the drive shaft 12 with a magnet coupling 15 is also shown, said coupling permitting the transmission of a drive movement from a motor 16 to the inside of a container 17, in which the drive shaft 12 is coupled to the magnet coupling.

The container 17 moreover serves as a rinsing device with several rinsing openings 18, 19, wherein a rinsing fluid, for example saline solution, is introduced through the opening 18 into the container 17 and excess rising fluid is removed through the second rinsing opening 19. The rinsing fluid moreover moves along the catheter 8 in the direction of the pump 4 and in particular on operation of the rotor, i.e. with a rotation of the drive shaft 12, is delivered by way of the spiral-like outer contour of the drive shaft 12, in the direction of the pump 4. Thus for trial operation, rinsing fluid can be fed through the first rinsing opening 18 and be moved through the catheter 8 to the pump 4, whilst this is located in the first receiving space 3, and the pump can then be operated for testing at least with a reduced speed whilst being wetted by the rinsing fluid.

FIG. 5 in a plan view from the top shows a first closure element 5' as well as the inside of the first receiving space 3, in which a heart pump 4 is arranged. The catheter 8 which is connected to the heart pump 4 projects through the opening 7 and outside the receiving space 3 in front of the opening 7 is surrounded by a sheath element 11. The sheath element 11 is designed for example of a flexible plastic torus in the form of a hose section which can have a predetermined breakage location, so that as a peel-away sheath, it can be radially pulled away at a later stage after bringing the pump 4 into an introduction sheath on the patient body.

The sheath elements 11 can be applied from the outside onto the edge of the opening 7 on the closure elements 5', 6' of the first receiving space 3, and on this, the pump 4 can be pulled out of the receiving space 3 in the direction of the arrow 20 by way of the catheter. The pump 4 is radially compressed on pulling into the opening 7 in the direction of the arrows 21, 22 due to the given diameter of the opening 7 which is smaller than the pump diameter in the expanded condition and in the compressed or at least partly compressed condition is pulled into the sheath element 11. There, it is again protected from contact and contamination and can be removed from the container 1' and be moved to an introduction sheath on the body of a patient.

FIG. 6 once again in a lateral view schematically shows a container 1' with a first receiving space 3, in which a pump 4 is arranged, as well as a sheath element 11 which is arranged in a groove 13 of the container 1' and which surrounds the catheter 8.

FIG. 7 in a further view seen in the direction of arrow 23 in FIG. 6 shows an outer view of the closure elements 5', 6' with the opening 7 and a plan view upon the sheath element 11 in the axial direction, as well as in a dashed representation the heart pump 4 lying in the first receiving space 3.

FIG. 8 in a perspective view shows a first closure element 5' which is designed as part of a blister, with two troughs, of which a first trough 24 is delimited by the first closure element 5' and forms the lower part of the first receiving space for a heart pump, whereas the second trough 25 delimits a third receiving space for a grip on the catheter 8. A groove 13 can moreover be recognised, and this leads from the first trough 24 to the second trough 25, forms a second receiving space and permits the deposition of a catheter, wherein an arched additional groove 13a is also formed and this permits the deposition of loops of the catheter. Grip recesses 27, 28 are moreover provided in the region of the groove 13 which on the one hand serve for the stabilisation of the blister and on the other hand serve for the improved gripping of a catheter located in the groove 13, on removal, as well as for forming protrusions of the blister which can serve as support elements on placing onto a level surface next to the troughs 24, 25.

A heart pump 4 as well as the grip part 26 is represented within the container 1" or the closure element 5'. Usually however, a closure element is provided on the first trough 24 as well as on the second trough 25, in order to cover the respective troughs and the components which are located therein, and to protect these from contact as well as to fix the components in a vibration-secure manner and this completes the container 1". For this reason, the atraumatic tip of the catheter (co-called pigtail tip) is also fixed, such that it does not permit excessive movements of the pump head, but on the other hand a withdrawal in the direction of the sheath element 11 is not inhibited.

A cross section through the trough 24 is represented by way of example in FIG. 9 and this is formed in the first closure element 5' which is formed as part of a blister. A prominence 29 is formed by a suitable prominent arching of the closure element 5', within the trough and within the first receiving space 3, wherein the prominence 29 comprises a recess 30 per se which within the first receiving space 3 receives the heart pump 4. An accurate, tight and forced positioning of the heart pump 4 in the first receiving space 3 is given by this. The first receiving space 3 is moreover completely covered by a second closure element 6" in the form of a stiff plastic foil, wherein the second closure element 6" in the region of the contact surface to the first closure element 5' can be bonded, welded or pressed to this (for example also by way of connection similar to a push button), so that a detachment of the second closure element 6" is not possible or only very difficultly possible, without a destruction of the container 1". The open sides of the first and the second closure element 5', 6" in this example are directed in the same directions and do not face one another as would basically also be possible.

The cover shape of the closure element covering the second trough 25 can be designed similarly to the shape of the second closure element 6".

On preparing an implantation of a heart pump, as is represented in FIG. 8, firstly one bleeds and wets this and then the heart pump 4, on the catheter or on the grip 26 is pulled through the opening 7 out of the closed first receiving space 3 and pulled into a sheath element which is located outside the first receiving space. Thereby, the pump 4 is radially compressed. Thereafter it is reliably held in the sheath element 11 and is held in a manner protected from contact by the user.

The pump 4 can be operated on a trial basis before withdrawing out of the first receiving space, by way of a rinsing fluid being moved from a rinsing system located in the grip region, through rinsing openings, via the catheter 8 to the pump and this pump thereafter being driven by way of the flexible drive shaft, at a speed which is significantly reduced compared to operational speeds.

An arrangement as is represented in FIG. 9 as a cross-sectional representation is once again represented in a similar form in a three-dimensional representation in FIG. 10.

The container 1, 1', 1" (or 11''', see FIG. 11b) with the help of the invention and in the described manner can ensure a high degree of availability and operational reliability as well as sterility of the heart pump on implantation.

FIGS. 11a and 11b show further embodiments of receiving spaces. A receiving space is firstly shown therein in FIG. 11a, with which a joining location 9 is arranged in the horizontal direction (in the direction of a groove 13 or of a corresponding catheter). A joining location 9''' is additionally provided perpendicularly to this. These joining locations 9 and 9''' can be provided per se or also in a cumulative manner. Closure elements 5''' as well as 6''' are accordingly provided. A further opening 7a''' whose diameter is significantly greater than the diameter of the opening 7 is provided on the right side (opposite the opening 7). The size is dimensioned such that a heart pump can be pulled in, in the expanded or also in a slightly compressed condition 7a''. However, the heart pump after a closure of the opening 7a'' can then only be pulled out through the opening 7 amid compression. For this case, it is possible to provide a cover on the opening 7a'', which cannot be released in a destruction-free manner. Alternatively, one can also envisage a destruction-free decoupling of the cover (for example for overhaul by the manufacturer). The receiving space 3" or the capture basin 14" is to be designed according to the embodiments described above. The same applies to the remaining elements, which have already been dealt with above (for example the groove 13, a catheter 8, a heart pump 4, etc.).

FIG. 11b shows a further embodiment which differs from that in FIG. 11a in that here only one joining location 9''' is provided. Moreover, the lower closure element (indicated here at 5") is designed in a less solid manner The capture basin 14''' or the receiving space 3''' are basically as described above, and the same applies to the opening 7, the groove 13 as well as the catheters or heart pumps which are to be brought into the receiving space. A cover is shown in FIG. 11b (hatched) and this cover cannot be released from the closure elements 5''', 6''' in a destruction-free manner. The heart pump 4 which is accommodated in the receiving space 3''' is represented by way of example in the embodiment shown in FIG. 11b. From this, it is clear that the heart pump can be brought through the opening 7a''' into the receiving space, but can only be removed through the opening 7 amid compression. The embodiments which are shown in the FIGS. 11a and 11b can of course also be provided without a second opening or cover, and in this case the opening 7 is the only opening of the receiving spaces 3" and 3'''. In FIG. 11b, it is at least indicted that the heart pump 4 lies in the receiving space 3''' in the expanded condition, and that this expanded condition has such a diameter that the pump can pass through the opening 7a''' in an essentially compression-free manner, but can only pass the opening 7 under compression.

In some cases, it is then possible for the grip part 26 not to be assembled until after the heart pump has been brought into the receiving space 3, 3', 3", 3'''. The removal of the pump is possible without destruction only in the described manner, after assembly of the grip.

The invention claimed is:

1. A container housing a compressible and expandable heart pump, the container comprising:
   a first receiving space at least partially enclosing the compressible and expandable heart pump,
   wherein the first receiving space is delimited on all sides by one or more closure elements and the first receiving space is closed off to an outside and configured to prevent contacting the compressible and expandable heart pump,
   wherein the one or more closure elements are configured as two half-shell-shaped closure elements joined together to form the first receiving space;
   wherein the closure elements leave free first and second openings, the first opening sized for the passage of a catheter from the outside into the first receiving space,
   wherein the diameter of the first opening is sized such that the compressible and expandable heart pump is compressed during extraction of the compressible and expandable heart pump through the first opening.

2. A container according to claim 1, wherein at least the closure elements consist essentially of a plastic material.

3. A container according to claim 1, wherein the closure elements are undetachably connected to one another.

4. A container according to claim 1, wherein the first opening is formed for the extraction of the catheter between two closure elements.

5. A container according to claim 1, wherein a first closure element is configured as part of a blister package which receives at least the catheter.

6. A container according to claim 5, wherein the first closure element in a region of the first receiving space forms a capture shell configured to retain a fluid.

7. A container according to claim 1, wherein the first opening at least partly consists of a cylinder-symmetrical channel.

8. A container according to claim 7, wherein the cylinder-symmetrical channel narrows outwardly from an inside of the first receiving space.

9. A container according to claim 8, wherein a run-out of the first opening to an outer side of the closure elements comprises an edge, on which a hollow-cylindrical sheath element can be supported in the axial direction of the channel, wherein the hollow-cylindrical sheath element is configured to be displaceable along the catheter.

10. A container according to claim 1, further comprising:
the compressible and expandable heart pump coupled to the catheter and housed in the container, where the compressible and expandable heart pump is located in the first receiving space and wherein the catheter which is coupled to the compressible and expandable heart pump projects through the first opening out of the first receiving space; and
a sheath element through which the catheter passes; the sheath element provided on the catheter in a freely displaceable manner.

11. A container according to claim 1, wherein the first receiving space is delimited by at least two closure elements which are joined along a joining line, wherein the joining line runs essentially perpendicularly to a passing direction of the compressible and expandable heart pump.

12. A container according to claim 1, wherein the first receiving space is delimited by at least two closure elements which are joined along a joining line, wherein the joining line runs in a cross section of the receiving space which is larger than the cross section of the first opening for the passage of a catheter on removal of the compressible and expandable heart pump.

13. A container according to claim 1, wherein at least one of the openings is closed by a cover which is joined in a manner in which it is removable with or without destruction.

14. A container according to claim 1, wherein a diameter of the second opening is sized such that the compressible and expandable heart pump can be introduced into the receiving space without compression.

15. A container according to claim 1, wherein the first opening has a diameter of less than 4 mm.

16. The container according to claim 1, wherein the closure elements consist of a plastic foil.

17. A system for housing a compressible and expandable heart pump, the system comprising:
the compressible and expandable heart pump;
a container configured to house the compressible and expandable heart pump, the container comprising:
a first receiving space for the compressible and expandable heart pump,
wherein the first receiving space is delimited on all sides by one or more closure elements and the first receiving space is closed off to an outside and configured to prevent contacting the compressible and expandable heart pump,
wherein the one or more closure elements are configured as two half-shell-shaped closure elements joined together to form the first receiving space;
wherein the closure elements leave free an opening sized for the passage of a catheter from the outside into the first receiving space,
wherein the diameter of the opening is sized such that the compressible and expandable heart pump is compressed during extraction of the compressible and expandable heart pump through the opening.

18. A container housing a compressible and expandable heart pump, the container comprising:
a first receiving space at least partially enclosing the compressible and expandable heart pump,
wherein the first receiving space is delimited on all sides by one or more closure elements and the first receiving space is closed off to an outside and configured to prevent contacting the compressible and expandable heart pump,
wherein the one or more closure elements are configured as two half-shell-shaped closure elements joined together to form the first receiving space,
wherein the closure elements leave free an opening sized for the passage of a catheter from the outside into the first receiving space,
wherein the diameter of the opening is sized such that the compressible and expandable heart pump is compressed during extraction of the compressible and expandable heart pump through the opening,
wherein the opening at least partly consists of a cylinder-symmetrical channel that narrows outwardly from an inside of the first receiving space,
wherein a run-out of the opening to an outer side of the closure elements comprises an edge, on which a hollow-cylindrical sheath element can be supported in the axial direction of the channel, wherein the hollow-cylindrical sheath element is configured to be displaceable along the catheter.

19. A container housing a compressible and expandable heart pump, the container comprising:
a first receiving space at least partially enclosing the compressible and expandable heart pump; and
a sheath element,
wherein the first receiving space is delimited on all sides by one or more closure elements and the first receiving space is closed off to an outside and configured to prevent contacting the compressible and expandable heart pump,
wherein the one or more closure elements are configured as two half-shell-shaped closure elements joined together to form the first receiving space,
wherein the closure elements leave free an opening sized for the passage of a catheter from the outside into the first receiving space,
wherein the compressible and expandable heart pump is coupled to the catheter and located in the first receiving space and the catheter projects through the opening out of the first receiving space,
wherein the catheter passes through the sheath element and the sheath element is provided on the catheter in a freely displaceable manner,
wherein the diameter of the opening is sized such that the compressible and expandable heart pump is compressed during extraction of the compressible and expandable heart pump through the opening.

* * * * *

UNITED STATES PATENT AND TRADEMARK OFFICE
CERTIFICATE OF CORRECTION

PATENT NO. : 10,842,922 B2
APPLICATION NO. : 15/543006
DATED : November 24, 2020
INVENTOR(S) : Daniel Roehn et al.

It is certified that error appears in the above-identified patent and that said Letters Patent is hereby corrected as shown below:

In the Specification

Column 6, Line 39:
Now reads: "blister"; should read -- blister, --

Column 6, Line 41:
Now reads: "as"; should read -- as, --

Column 7, Line 33:
Now reads: "8"; should read -- 4 --

Column 8, Line 23:
Now reads: "5' 6'"; should read -- 5', 6" --

In the Claims

Column 10, Claim 2, Line 45:
Now reads: "A"; should read -- The --

Column 10, Claim 3, Line 47:
Now reads: "A"; should read -- The --

Column 10, Claim 4, Line 49:
Now reads: "A"; should read -- The --

Column 10, Claim 5, Line 52:
Now reads: "A"; should read -- The --

Column 10, Claim 6, Line 55:
Now reads: "A"; should read -- The --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,842,922 B2

Column 10, Claim 7, Line 58:
Now reads: "A"; should read -- The --

Column 10, Claim 8, Line 61:
Now reads: "A"; should read -- The --

Column 10, Claim 9, Line 64:
Now reads: "A"; should read -- The --

Column 11, Claim 10, Line 3:
Now reads: "A"; should read -- The --

Column 11, Claim 11, Line 14:
Now reads: "A"; should read -- The --

Column 11, Claim 12, Line 19:
Now reads: "A"; should read -- The --

Column 11, Claim 13, Line 26:
Now reads: "A"; should read -- The --

Column 11, Claim 14, Line 29:
Now reads: "A"; should read -- The --

Column 11, Claim 15, Line 33:
Now reads: "A"; should read -- The --